United States Patent
Humphreys et al.

(10) Patent No.: US 9,980,810 B2
(45) Date of Patent: May 29, 2018

(54) SYSTEM CONTROLLER FOR VARIABLE-OPTIC ELECTRONIC OPHTHALMIC LENS

(71) Applicant: Johnson & Johnson Vision Care, Inc., Jacksonville, FL (US)

(72) Inventors: Scott Robert Humphreys, Greensboro, NC (US); Adam Toner, Jacksonville, FL (US); Randall Braxton Pugh, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 554 days.

(21) Appl. No.: 13/780,707

(22) Filed: Feb. 28, 2013

(65) Prior Publication Data

US 2013/0261743 A1 Oct. 3, 2013

Related U.S. Application Data

(60) Provisional application No. 61/619,727, filed on Apr. 3, 2012, provisional application No. 61/619,655, filed on Apr. 3, 2012.

(51) Int. Cl.
*G02C 1/00* (2006.01)
*G02C 7/00* (2006.01)
(Continued)

(52) U.S. Cl.
CPC ............. *A61F 2/1624* (2013.01); *G02C 7/04* (2013.01); *G02C 7/083* (2013.01)

(58) Field of Classification Search
CPC .......... G02C 7/04; G02C 7/083; G02C 7/048; G02C 7/085; G02C 11/10; A61F 2/16;
(Continued)

(56) References Cited

U.S. PATENT DOCUMENTS

| 6,885,818 B2 | 4/2005 | Goldstein | |
| 2006/0146281 A1* | 7/2006 | Goodall | G02B 3/14 |
| | | | 351/159.02 |

(Continued)

FOREIGN PATENT DOCUMENTS

| CN | 101791259 A | 8/2010 |
| CN | 1022271899 A | 12/2011 |

(Continued)

OTHER PUBLICATIONS

Search Report from Hungarian Patent Office dated May 8, 2014 for Application No. 201302102-7.

(Continued)

*Primary Examiner* — Mustak Choudhury (57) ABSTRACT

A system controller for an ophthalmic lens comprising an electronic system which actuates a variable-focus optic is disclosed herein. The system controller is part of an electronic system incorporated into the ophthalmic lens. The electronic system includes one or more batteries or other power sources, power management circuitry, one or more sensors, clock generation circuitry, control algorithms and circuitry, and lens driver circuitry. The controller including multiple state machines configured as digital logic gates.

24 Claims, 8 Drawing Sheets

(51) Int. Cl.
  *G02C 7/02* (2006.01)
  *G02C 7/04* (2006.01)
  *A61F 2/16* (2006.01)
  *G02C 7/08* (2006.01)

(58) Field of Classification Search
  CPC ...... A61F 2/145; A61F 2/1627; A61F 2/1635;
        B29D 11/00038; B29D 11/00826; B29D
        11/00009; B29D 11/00028; B29D
        11/00951; B29D 11/00961; G02B 3/14
  USPC .... 351/159.39, 159.02, 159.03, 159.05, 168,
        351/159.75, 219, 159.34, 210; 359/642;
        623/6.11, 6.22; 264/1.38; 425/126.1,
        425/174.4
  See application file for complete search history.

(56) References Cited

U.S. PATENT DOCUMENTS

| | | |
|---|---|---|
| 2010/0076553 A1 | 3/2010 | Pugh et al. |
| 2010/0110372 A1* | 5/2010 | Pugh ............... B29D 11/00009 351/159.75 |
| 2012/0268712 A1* | 10/2012 | Egan ................. G02C 7/085 351/159.34 |

FOREIGN PATENT DOCUMENTS

| | | |
|---|---|---|
| EP | 1760515 A2 | 3/2007 |
| EP | 1760516 A1 | 3/2007 |
| JP | 2007511797 A | 5/2007 |
| JP | 2010537777 A | 12/2010 |
| JP | 2012507748 A | 3/2012 |
| JP | 2013541049 A | 11/2013 |
| TW | 201026489 A | 7/2010 |
| TW | 201029830 A | 8/2010 |
| WO | WO 10/051225 A9 | 5/2010 |
| WO | WO 11/067391 A1 | 6/2011 |
| WO | WO2011067391 A1 | 6/2011 |
| WO | WO 11/163080 A1 | 12/2011 |
| WO | WO2012051167 A1 | 4/2012 |

OTHER PUBLICATIONS

European Search Report for corresponding Application No. EP13162181 dated Jul. 22, 2013.

* cited by examiner

SYSTEM CONTROLLER FOR VARIABLE-OPTIC ELECTRONIC OPHTHALMIC LENS

CROSS REFERENCE TO RELATED APPLICATIONS

This patent application claims the benefit of U.S. Provisional Patent Application No. 61/619,727, filed Apr. 3, 2012 and U.S. Provisional Patent Application No. 61/619,655, filed Apr. 3, 2012.

BACKGROUND OF THE INVENTION

1. Field of the Invention

The present invention relates to a variable-optic powered or electronic ophthalmic lens, and more particularly to a system controller for controlling a variable-optic electronic ophthalmic lens.

2. Discussion of the Related Art

As electronic devices continue to be miniaturized, it is becoming increasingly more likely to create wearable or embeddable microelectronic devices for a variety of uses. Such uses may include monitoring aspects of body chemistry, administering controlled dosages of medications or therapeutic agents via various mechanisms, including automatically, in response to measurements, or in response to external control signals, and augmenting the performance of organs or tissues. Examples of such devices include glucose infusion pumps, pacemakers, defibrillators, ventricular assist devices and neurostimulators. A new, particularly useful field of application is in ophthalmic wearable lenses and contact lenses. For example, a wearable lens may incorporate a lens assembly having an electronically adjustable focus to augment or enhance the performance of the eye. In another example, either with or without adjustable focus, a wearable contact lens may incorporate electronic sensors to detect concentrations of particular chemicals in the precorneal (tear) film. The use of embedded electronics in a lens assembly introduces a potential requirement for communication with the electronics, for a method of powering and/or re-energizing the electronics, for interconnecting the electronics, for internal and external sensing and/or monitoring, and for control of the electronics and the overall function of the lens.

The human eye has the ability to discern millions of colors, adjust easily to shifting light conditions, and transmit signals or information to the brain at a rate exceeding that of a high-speed internet connection. Lenses, such as contact lenses and intraocular lenses, currently are utilized to correct vision defects such as myopia (nearsightedness), hyperopia (farsightedness), presbyopia and astigmatism. However, properly designed lenses incorporating additional components may be utilized to enhance vision as well as to correct vision defects.

Contact lenses may be utilized to correct myopia, hyperopia, astigmatism as well as other visual acuity defects. Contact lenses may also be utilized to enhance the natural appearance of the wearer's eyes. Contact lenses or "contacts" are simply lenses placed on the anterior surface of the eye. Contact lenses are considered medical devices and may be worn to correct vision and/or for cosmetic or other therapeutic reasons. Contact lenses have been utilized commercially to improve vision since the 1950s. Early contact lenses were made or fabricated from hard materials, were relatively expensive and fragile. In addition, these early contact lenses were fabricated from materials that did not allow sufficient oxygen transmission through the contact lens to the conjunctiva and cornea which potentially could cause a number of adverse clinical effects. Although these contact lenses are still utilized, they are not suitable for all patients due to their poor initial comfort. Later developments in the field gave rise to soft contact lenses, based upon hydrogels, which are extremely popular and widely utilized today. Specifically, silicone hydrogel contact lenses that are available today combine the benefit of silicone, which has extremely high oxygen permeability, with the proven comfort and clinical performance of hydrogels. Essentially, these silicone hydrogel based contact lenses have higher oxygen permeability and are generally more comfortable to wear than the contact lenses made of the earlier hard materials.

Conventional contact lenses are polymeric structures with specific shapes to correct various vision problems as briefly set forth above. To achieve enhanced functionality, various electronic circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contract lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low-light conditions. The properly designed electronics and/or arrangement of electronics on lenses may allow for projecting an image onto the retina, for example, without a variable-focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This, coupled with a wireless data transmitter, could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The proper combination of devices could yield potentially unlimited functionality; however, there are a number of difficulties associated with the incorporation of extra components on a piece of optical-grade polymer. In general, it is difficult to manufacture such components directly on the lens for a number of reasons, as well as mounting and interconnecting planar devices on a non-planar surface. It is also difficult to manufacture to scale. The components to be placed on or in the lens need to be miniaturized and integrated onto just 1.5 square centimeters (assuming a lens with a 7 mm radius) of a transparent polymer while protecting the components from the liquid environment on the eye. It is also difficult to make a contact lens comfortable and safe for the wearer with the added thickness of additional components.

More specifically, the 1.5 square centimeters of transparent polymer represents the entire area of the contact lens. In certain exemplary embodiments, it is preferable that the electronics be in the periphery of the lens and out of the optic zone. Alternate exemplary embodiments are also possible utilizing thin-film materials or transparent silicon. In the above example, if the center eight (8) mm diameter portion (4 mm radius) is reserved for the optic zone, then at most one (1) square centimeter is left for the electronics. Future designs may offer even less area for electronics, for example, there may be designs with annular rings of about 0.17 square centimeters (17 square millimeters) not including the variable-focus optic. What this means is that a maximum IC die area of just 1.26 square millimeters for a given die may be available to work with. In other words, what is needed in the present invention is a design and configuration of an unprecedented scale.

Given the area and volume constraints of an ophthalmic device such as a contact lens, and the environment in which it is to be utilized, the physical realization of the device must overcome a number of problems, including mounting and interconnecting a number of electronic components on a non-planar surface, the bulk of which comprises optic plastic. Accordingly, there exists a need for providing a mechanically and electrically robust electronic contact lens.

As these are powered lenses, energy or more particularly current and power consumption, to run the electronics is a concern given battery technology on the scale for an ophthalmic lens. In addition to normal current consumption, powered devices or systems of this nature generally require standby current reserves, precise voltage control and switching capabilities to ensure operation over a potentially wide range of operating parameters, and burst consumption, for example, up to eighteen (18) hours on a single charge, after potentially remaining idle for years. Accordingly, there exists a need for a system that is optimized for low-cost, long-term reliable service, safety and size while providing the required power.

In addition, because of the complexity of the functionality associated with a powered lens and the high level of interaction between all of the components comprising a powered lens, there is a need to coordinate and control the overall operation of the electronics and optics comprising a powered ophthalmic lens. Commercial microcontrollers have been considered for the control of electronic ophthalmic devices; however, the microcontrollers currently available have a number of drawbacks for use in an electronic ophthalmic device. These microcontrollers are currently about five (5) square millimeters, with edge dimensions longer than permitted in some ophthalmic device designs and die thickness on the order of hundreds of microns, again too large for an ophthalmic device. Commercial microcontrollers are not specifically tailored to the requirements of an ophthalmic electronic system, and thus may contain functional blocks not required, wasting space and current, or not contain required functional blocks. Other limitations prevent commercially available microcontrollers and other off-the-shelf electronic components from being utilized in electronic ophthalmic devices. Accordingly, there is a need for a system to control the operation of all of the other components that is safe, low-cost, and reliable, has a low rate of power consumption and is scalable for incorporation into an ophthalmic lens.

Powered lens systems may incorporate power storage devices (batteries) having a high series resistance and low capacity. Prior art circuits such as commercially available microcontrollers require peak and average currents too high for this type of power source, such that the peak currents would lead to an unacceptable drop in the battery output voltage and the average current would deplete the battery charge too rapidly for the required battery life of the powered lens system.

Accordingly, there is a need for a system controller capable of providing flexible operation of the electronic and electromechanical or electrochemical systems embedded in the powered lens that is designed and configured to minimize the overall power consumption of the system. The system controller should be responsive to changing conditions both external to and within the powered lens so as to provide an optimal combination of functionality or performance while minimizing power consumption. In addition the system controller should preferably require or consume a volume and area small enough for integration into a contact lens along with other required components.

SUMMARY OF THE INVENTION

The system controller, including the electronic circuitry and control algorithms for controlling a variable optic ophthalmic lens, of the present invention overcomes the disadvantages associated with the prior art as briefly described above.

The present invention relates to a powered contact lens comprising an electronic system, which performs any number of functions, including actuating a variable-focus optic. The electronic system includes one or more batteries or other power sources, power management circuitry, one or more sensors, clock generation circuitry, control circuitry implementing suitable control algorithms, and lens driver circuitry. The system may further comprise circuits that perform blink detection via incident light or other electromagnetic waves or fields.

In accordance with one aspect, the present invention is directed to an ophthalmic apparatus. The ophthalmic apparatus comprises an electronic system incorporated into an ophthalmic device configured for use in at least one of in or on the eye, a system controller incorporated into the electronic system for controlling the operation thereof, the system controller being configured to implement a master state machine that receives at least one signal and outputs at least one signal, electronic circuitry incorporated into the electronic system, the electronic circuitry being operatively associated with and providing power to the system controller, the electronic circuitry including one or more power sources and one or more of clock generation circuits or inputs, and at least one actuator configured to receive the at least one output from the system controller.

The system controller comprises a set of state machines, implemented in digital logic, which controls components of the system. The system controller may receive power, bias and one or more clock signals from the power management circuitry and the clock generation circuitry. The system controller executes pre-determined or pre-programmed operations which are designed into the digital logic. The system controller performs a number of functions, including triggering one or more sensors to acquire one or more samples of signals provided by the one or more sensors (sensor inputs), storing sensor inputs, comparing sensor inputs to programmed patterns, determining the next action to take and the next state of the system based upon the current state of the system and the sensor inputs or stored sensor inputs, and activating and deactivating other components comprising the system. The system controller may also be programmed through various interfaces to alter its operation.

The system controller of the present invention offers a safe, low-cost, reliable means for controlling a variable-optic electronic contact lens which also has a low rate of power consumption and is scalable in area, volume and the like for incorporation into an ophthalmic device, such as a contact lens, without significant impact on comfort or wearability.

BRIEF DESCRIPTION OF THE DRAWINGS

The foregoing and other features and advantages of the invention will be apparent from the following, more particular description of preferred embodiments of the invention, as illustrated in the accompanying drawings.

DETAILED DESCRIPTION OF THE PREFERRED EMBODIMENTS

Conventional contact lenses are polymeric structures with specific shapes to correct various vision problems as briefly set forth above. To achieve enhanced functionality, various circuits and components have to be integrated into these polymeric structures. For example, control circuits, microprocessors, communication devices, power supplies, sensors, actuators, light-emitting diodes, and miniature antennas may be integrated into contact lenses via custom-built optoelectronic components to not only correct vision, but to enhance vision as well as provide additional functionality as is explained herein. Electronic and/or powered contact lenses may be designed to provide enhanced vision via zoom-in and zoom-out capabilities, or just simply modifying the refractive capabilities of the lenses. Electronic and/or powered contact lenses may be designed to enhance color and resolution, to display textural information, to translate speech into captions in real time, to offer visual cues from a navigation system, and to provide image processing and internet access. The lenses may be designed to allow the wearer to see in low light conditions. The properly designed electronics and/or arrangement of electronics on lenses may allow for projecting an image onto the retina, for example, without a variable focus optic lens, provide novelty image displays and even provide wakeup alerts. Alternately, or in addition to any of these functions or similar functions, the contact lenses may incorporate components for the noninvasive monitoring of the wearer's biomarkers and health indicators. For example, sensors built into the lenses may allow a diabetic patient to keep tabs on blood sugar levels by analyzing components of the tear film without the need for drawing blood. In addition, an appropriately configured lens may incorporate sensors for monitoring cholesterol, sodium, and potassium levels, as well as other biological markers. This coupled with a wireless data transmitter could allow a physician to have almost immediate access to a patient's blood chemistry without the need for the patient to waste time getting to a laboratory and having blood drawn. In addition, sensors built into the lenses may be utilized to detect light incident on the eye to compensate for ambient light conditions or for use in determining blink patterns.

The powered or electronic contact lens of the present invention comprises the necessary elements to correct and/or enhance the vision of patients with one or more of the above described vision defects or otherwise perform a useful ophthalmic function. In addition, they may be utilized simply to enhance normal vision or provide a wide variety of functionality as described above. The electronic contact lens may comprise a variable focus optic lens, an assembled front optic embedded into a contact lens or just simply embedding electronics without a lens for any suitable functionality. The electronic lens of the present invention may be incorporated into any number of contact lenses as described above. In addition, intraocular lenses may also incorporate the various components and functionality described herein. However, for ease of explanation, the disclosure will focus on an electronic contact lens to correct vision defects intended for single-use daily disposability.

Throughout the specification the terms ophthalmic device and ophthalmic device are utilized. In general terms, an ophthalmic device may include contact lenses, intraocular lenses, spectacle lenses and punctal plugs. However, in accordance with the present invention, an ophthalmic device is one for eye disease treatment, vision correction and/or enhancement and preferably includes at least one of punctal plugs, spectacle lenses, contact lenses and intraocular lenses. An intraocular lens or IOL is a lens that is implanted in the eye and replaces the crystalline lens. It may be utilized for individuals with cataracts or simply to treat various refractive errors. An IOL typically comprises a small plastic lens with plastic side struts called haptics to hold the lens in position within the capsular bag in the eye. Any of the electronics and/or components described herein may be incorporated into IOLs in a manner similar to that of contact lenses. A punctal plug or occluder is an ophthalmic device for insertion into a punctum of an eye in order to treat one or more disease states. While the present invention may be utilized in any of these devices, in preferred exemplary embodiments, the present invention is utilized in contact lenses or intraocular lenses.

The present invention is directed to a powered ophthalmic lens or powered contact lens comprising an electronic system, which actuates a variable-focus optic or any other device or devices configured to implement any number of numerous functions that may be performed. The electronic system includes one or more batteries or other power sources, power management circuitry, one or more sensors, clock generation circuitry, control circuitry implementing suitable control algorithms, and lens driver circuitry. The complexity of these components may vary depending on the required or desired functionality of the lens.

It is important to note that the system controller of the present invention may receive any number of inputs for controlling a powered or electronic ophthalmic lens, for example, a contact lens comprising a variable power optic element or variable-focus optic for zooming in on distant objects and zooming out on close objects.

A system controller or control system comprises one or more devices configured to manage, command, direct and/or regulate the actions of other devices and/or systems. While there are a number of different types of control systems, they generally fall into two classes or types; namely, logic or sequential control systems and feedback or linear control systems. In a logic or sequential control system, command signals are output which trigger a series of actuators in a predetermined sequence to perform one or more tasks. In a feedback control system, a control loop, including one or more sensors, control algorithms, and actuators is configured to regulate a variable at a set point or reference value. In any feedback control system, one needs to know what the system is to do, to know how well the system is performing, and to use the performance information to correct and control the system.

The components of the basic feedback control system may be described as follows. The control system comprises the system or plant to be controlled and is configured to receive an input and provide an output. The output of the plant is input to a sensor which measures one or more parameters of the plant and provides a feedback signal. The feedback signal is then subtracted, via a comparator or other suitable means, from the input signal to generate an error signal. The error signal is then input to a controller which outputs a signal to the plant thereby causing the plant to implement the desired action. Essentially, the feedback from the sensor attempts to account for all of the complexities of the entire system and produces an output that is the desired result for a given input. All control systems are designed within the confines of certain control laws and typically represent tradeoffs in various aspects, including speed and accuracy. Although this description is overly simplified and described in terms of hardware, it provides the basis for feedback control systems which may be implemented in hardware, software or any combination thereof.

Feedback control systems may be further classified as proportional controllers, integral controllers, derivative controllers or combinations thereof. In a proportional controller, the control action is proportional to the error. In an integral controller, the actuating signal or input to the plant is proportional to the integral of the error. In a derivative controller, the output of the process is proportional to the rate at which the input changes. Each type of controller offers its own advantage as is known in the control art. For example, a steady state error should be achieved when utilizing an integral controller.

A sequential controller, as set forth above, is one in which a series of actions need to occur in a specific order. These actions may be quite complex, because all of the conditions of the overall process must be known. Sequential controllers generally comprise logic systems to sequence commands for controlling electrical and/or mechanical actions. Programmable logic controllers and microcontrollers may be programmed for sequential control.

The system controller of the present invention is primarily a sequential control system though it will be appreciated by the skilled artisan that the system controller or subsystems associated with the system controller may incorporate features to respond to feedback provided by sensor inputs. Examples of such operations may include altering a duty cycle or power level of a subsystem in response to lower battery capacity, adjusting an internal clock frequency to synchronize to a frequency associated with received signals, and/or regulating an amount of therapeutic agent or drug delivered to the tear film of the eye in response to a measurement of tear film chemistry.

As set forth above, the present invention relates to a contact lens comprising a number of components, with the system controller being one of these components. The proper combination of devices could yield potentially unlimited functionality; however, there are a number of difficulties associated with the incorporation of extra components on a piece of optical-grade polymer that makes up the contact lens. In general, it is difficult to manufacture such components directly on the lens for a number of reasons, as well as mounting and interconnecting planar devices on a non-planar surface. It is also difficult to manufacture to scale and form. The components to be placed on or in the lens need to be miniaturized and integrated onto just 1.5 square centimeters of a transparent polymer, or more particularly, seventeen (17) square millimeters, while protecting the components from the liquid environment on the eye. It is also difficult to make a contact lens comfortable and safe for the wearer with the added thickness of additional components.

In addition to the size requirements set forth herein, electronic devices incorporated into a contact lens have to be robust and safe for use in an essentially aqueous environment. Tears have a pH of about 7.4 and are about 98.2 percent water and 1.8 percent solids, including electrolytes such as sodium, potassium, calcium, magnesium, and chlorides. This is a somewhat harsh environment in which to introduce electronics. Also, contact lenses are generally designed to be worn for at least four hours and preferably longer than eight hours. Electronic components require energy. This energy may be supplied from any number of sources, including built-in batteries. Since batteries and other potential energy sources have limited potential at these sizes, all electronic components, including the system controller, are preferably designed to consume as little power as possible so that the contact lenses may be worn for a given period of time even after sitting idle for a given period of time (shelf life). Finally, all components in an electronic contact lens have to be biocompatible and safe. Accordingly, all electronics incorporated into the contact lens have to meet all of the above design parameters; namely, size, survivability in an aqueous solution, power consumption and safety. The system controller of the present invention meets all of these requirements.

Figure 1:
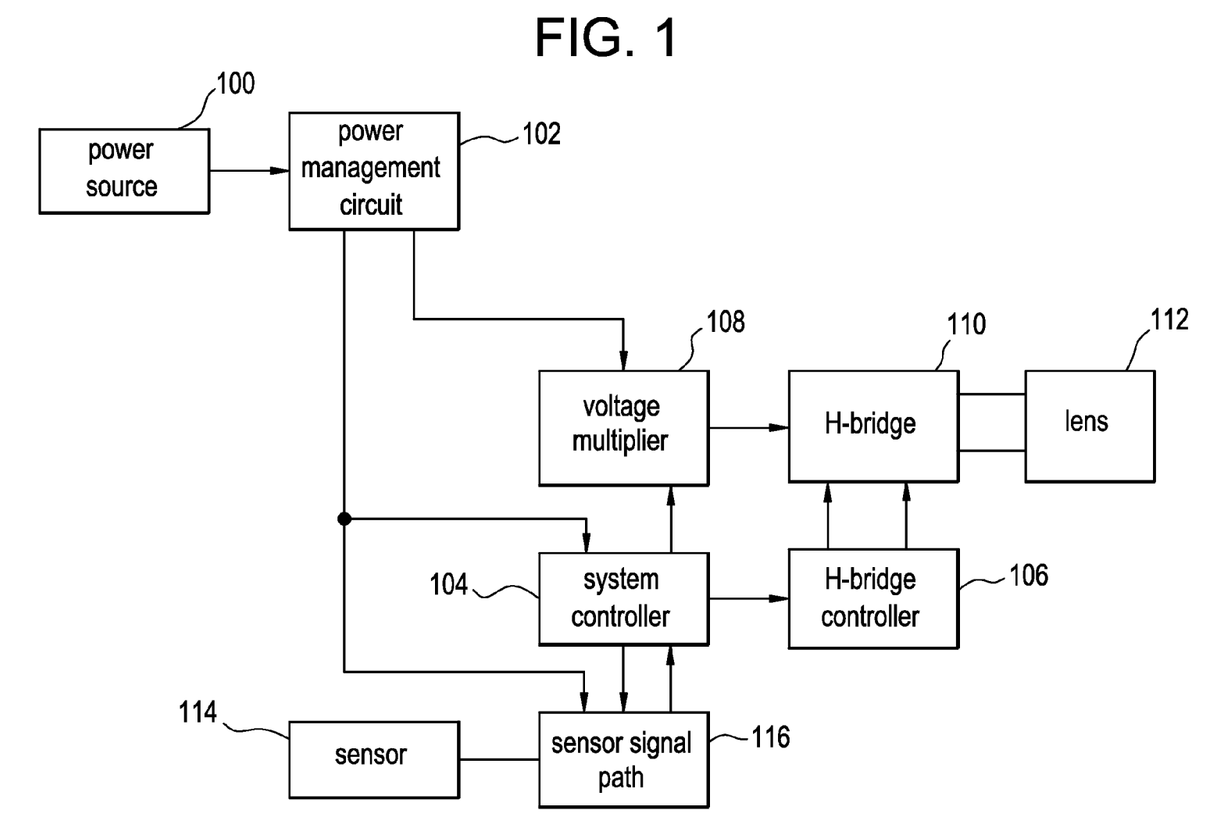
FIG. 1 is a block diagram representation of an exemplary variable-focus lens system in accordance with the present invention.

Referring now to FIG. 1, there is illustrated an exemplary embodiment of a variable-focus electronic ophthalmic lens system comprising a power source 100, a power management circuit 102, a system controller 104, an H-bridge-controller 106, a voltage multiplier 108, an H-bridge 110, a variable-focus optic 112, a sensor 114 and a sensor signal path 116. A detailed description of each of the components set forth above is given subsequently. It is important to note that each of the components described herein may be implemented in any number of suitable ways. It is also important to note that the functional blocks are shown and described for illustrative purposes, and that functional blocks may be added, removed, or substituted while still relying on the basic principles of a system controlled designed and configured specifically for use in an electronic or powered ophthalmic device as described herein:

The variable-focus ophthalmic optic or simply the variable-focus optic 112 may be a liquid lens that changes focal properties, e.g. focal length, in response to an activation voltage applied across two electrical terminals of the variable-focus optic 112. It is important to note, however, that the variable-focus lens optic may comprise any suitable, controllable optic device such as a light-emitting diode or microelectromechanical system (MEMS) actuator. The two terminals may correspond to a front-side and a back-side terminal of the variable-focus optic 112. The activation voltage may be significantly higher than voltages available from the power source; accordingly, there is a need for the other circuitry described herein. The power source 100 may comprise a battery, an energy harvester, a capacitor or any similar device providing current at a usable working voltage. In some exemplary embodiments, the power source 100 may be an inductive power coupling to an external power supply. The power management circuit 102 may comprise one or more voltage regulators, converters, voltage or current references, and switches to selectively enable power supplied to other components in the variable-focus electronic ophthalmic lens system. The system controller 104 provides control signals to the voltage multiplier 108 and to the H-bridge controller 106 based on an internal algorithm or under external control by a user (interface not shown). The voltage multiplier 108 receives current at a low working voltage from the power source 100 and generates a high output voltage at or above the activation voltage of the variable-focus optic 112, i.e. sufficient to change the state of the variable-focus optic 112. The voltage multiplier 108 may further comprise an oscillator or receive a clock signal from the system controller 104. In this exemplary embodiment, the voltage multiplier output is coupled to the variable-focus optic 112 through an H-bridge switch circuit 110, the H-bridge switch being a well known functional block of an electronic system. The H-bridge switch circuit 110 comprises switches between the voltage multiplier 108 and each of the variable-focus optic 112 terminals, and between each of the variable-focus optic 112 terminals and an electrical ground of the system. A state of the H-bridge switch circuit 110 is determined by one or more of the system controller 104 control signals. The H-bridge switch circuit 110 may be configured into one or more states, such as with the variable-focus optic 112 terminals open, shorted to ground, or powered with one terminal coupled to the voltage multiplier 108 and the other to ground, or powered in the opposite polarity. The system controller 104 may periodically reverse the polarity of the H-bridge switch circuit 110 output to optimize the performance of the variable-focus optic 112, for example, to avoid excessive charge trapping that may occur when powered in one state for too long.

The sensor 114 may be a light sensor such as a photodiode, a pressure sensor, a capacitive touch sensor, or an electromagnetic coil or antenna to sense radio frequency or low frequency electromagnetic signals. The sensor 114 may also comprise an eyelid position sensor, a pupil convergence sensor, a rear-facing pupil dilation sensor, an emitter-detector pair sensor, a blink detection sensor or any combination of sensors. The sensor signal path 116 comprises circuitry adapted to receive an output signal of the sensor 114 and process the signal to achieve desired noise filtering, amplification or other modifications and provide a conditioned sensor signal to the system controller 104. The sensor signal path 116 may be controlled by the system controller 104 such as to enable or disable the circuitry or modify operating parameters of the circuitry such as a gain or one or more filter corner frequencies. In some exemplary embodiments, the variable-focus electronic ophthalmic lens system may comprise one or more sensors and sensor signal paths of similar or different types.

The system controller 104 comprises a digital control system which controls components of the system and may be implemented as either a microcontroller running software or in digital logic such as one or more state machines. It is important to note that regardless of how the system controller 104 is implemented, it is designed and configured to be incorporated into a portion of a contact lens. Accordingly, size and power consumption are important factors. The system controller 104 may further comprise an oscillator for generating a periodic timing signal for the control system. The system controller 104 receives bias and power from the power management circuitry 102 and clock pulses from the clock generation circuitry (low frequency oscillator 202 illustrated in FIG. 2 described below). The low frequency oscillator 202 may be stand alone or part of the power management circuitry 102. The system controller 104 executes pre-determined or pre-programmed operations which are designed into the digital logic. The system controller 104 performs a number of functions, including triggering one or more sensors to acquire one or more samples, storing sensor inputs, comparing sensor inputs to programmed patterns, determining the next action to take based upon the current state of the system, and activating and deactivating other components comprising the system. The system controller 104 may also be programmed through various interfaces to alter its operation.

Figure 2:
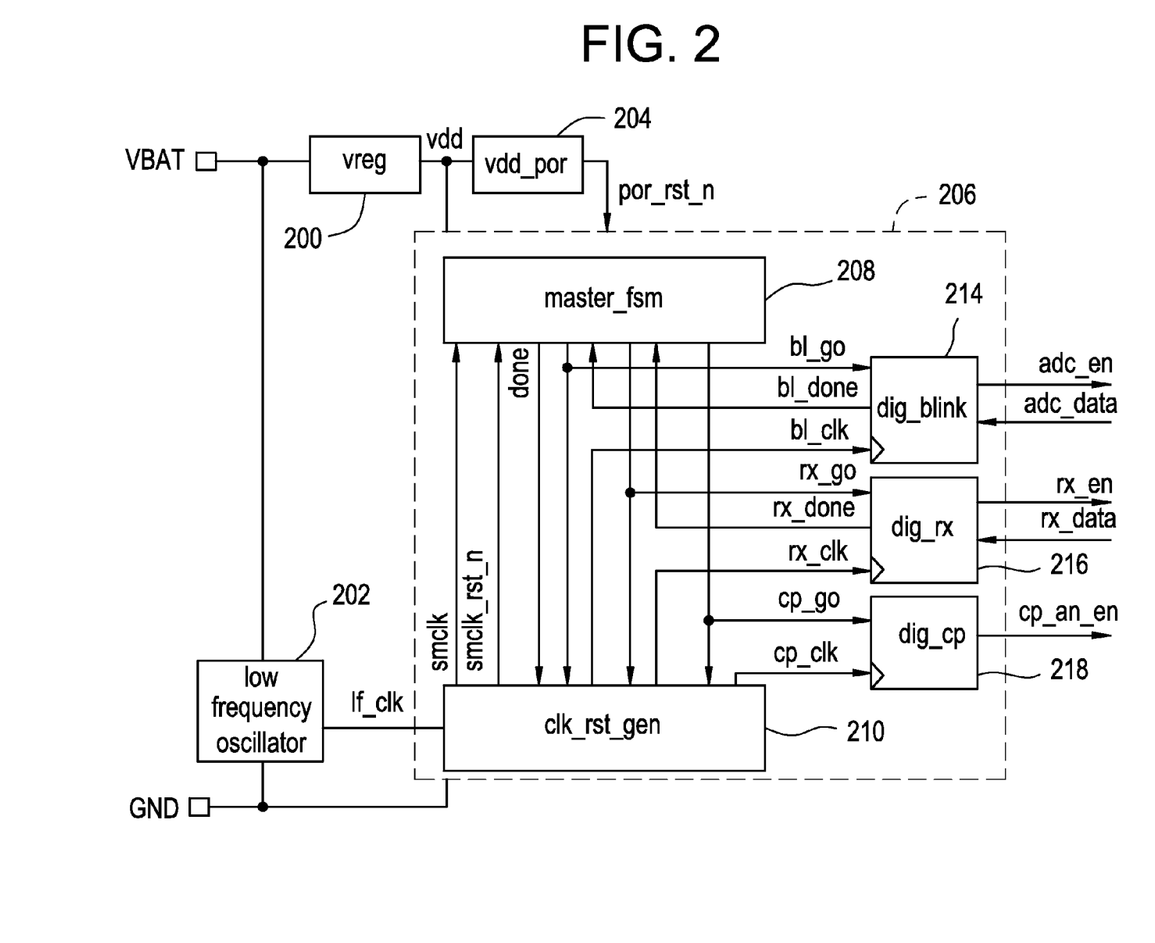
FIG. 2 is a block diagram representation of an integrated portion of the variable-focus lens system of FIG. 1.

FIG. 2 illustrates an exemplary embodiment of an integrated portion of a variable-focus electronic ophthalmic lens system, with particular detail provided for a system controller and related circuits that may be integrated together in a semiconductor die. The integrated portion of the variable-focus lens subsystem comprises a voltage regulator vreg 200, a low frequency oscillator 202, a regulator-based power-on reset circuit vdd_por 204, and a system controller 206.

The voltage regulator vreg 200 is coupled to a battery or external power source and provides a regulated voltage for other circuits in the system, in particular to the system controller 206. The regulator-based power-on reset circuit vdd_por 204 is coupled to the regulator output, provides a reset signal por_rst_n that indicates when the regulator output voltage is stable at a usable voltage level, and ensures that registers in the system controller 206 are reset to a desired default starting state at system power-up. The low frequency oscillator 202 provides a low frequency clock signal lf_clk to the system controller 206.

In this exemplary embodiment, the system controller 206 comprises a master state machine master_fsm 208, a clock and reset generator clk_rst_gen 210, a digital blink detection subsystem dig_blink 214, a digital receiver subsystem dig_rx 216, and a charge-pump voltage multiplier controller dig_cp 218. The clock and reset generator clk_rst_gen 210 receives the low frequency clock signal lf_clk and the regulator-based power-on reset signal por_rst_n and provides clocks and resets to the blocks in the system controller 206. The master state machine master_fsm 208 receives a state machine clock signal smclk and the state machine reset signal smclk_rst_n from the clock and reset generator clk_rst_gen 210. The master state machine master_fsm 208 comprises a state machine that progresses through a predetermined sequence of states in which other blocks in the system controller 206 are activated or enabled. The digital blink detection subsystem dig_blink 214 may comprise a state machine and additional logic to provide an enable signal adc_en to and receive data on a signal adc_data from an analog-to-digital converter. The digital receiver subsystem dig_rx 216 may comprise a state machine and additional logic to provide an enable signal rx_en to and receive data on a signal rx_data from a receiver subsystem. The receiver subsystem may comprise a separate sensor and sensor signal path in the variable-focus lens system. The charge-pump voltage multiplier controller dig_cp 218 may comprise logic to decode a latched or stored value in the system controller 206 and provide a charge pump enable signal cp_an_en to a charge pump voltage multiplier. The behavior of the signals and blocks illustrated in FIG. 2 are explained further in the descriptions of FIG. 3 and FIG. 4 subsequently.

Figure 3:
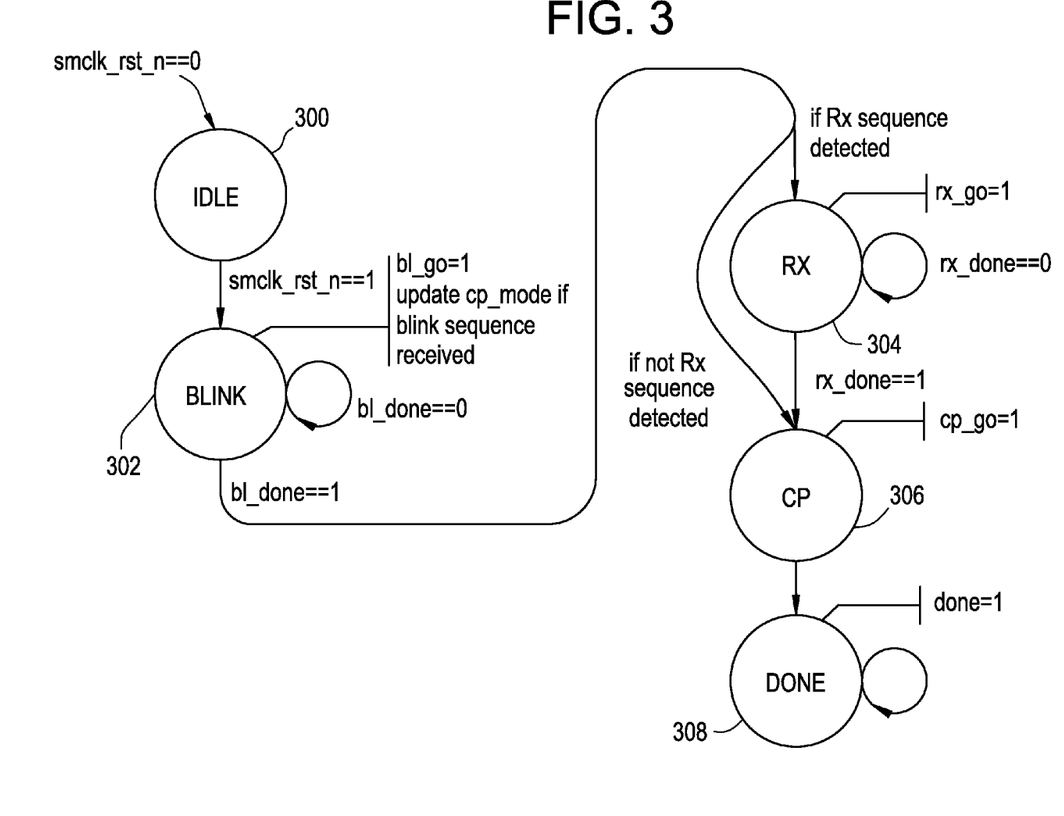
FIG. 3 is an exemplary state transition diagram for a master state machine of the system controller of the present invention.

FIG. 3 illustrates a state transition diagram for the master state machine master_fsm 208 of the exemplary embodiment illustrated in FIG. 2. The initial state is an IDLE state 300 in which the master state machine master_fsm 208 is placed when the reset signal smclk_rst_n from the clock and reset generator clk_rst_gen 210 is asserted (active low in this exemplary embodiment). On the first state machine clock edge on smclk the master state machine master_fsm 208 transitions to the BLINK state 302, during which the digital blink detection subsystem dig_blink 214 is enabled by assertion of a signal bl_go. The master state machine master_fsm 208 remains in the BLINK state 302 until a blink done signal bl_done is received from the digital blink detection subsystem dig_blink 214 indicating blink detection operations are complete. The master state machine master_fsm 208 may latch or store an output value of the digital blink detection subsystem dig_blink 214 into a register for further decoding or processing. The output value may be based on detection of a sequence of light levels or blink patterns that match a predetermined or programmable pattern. One pattern may be used to update the state of the charge-pump voltage multiplier controller dig_cp. Another pattern may be used to enter a communication reception mode. The master state machine master_fsm 208 then transitions, conditionally based on the value latched in the BLINK state 302, to either the RX state 304 or the CP state 306 as indicated in the diagram by the labels 'if Rx sequence detected' and 'if not Rx sequence detected.' In the RX state 304, the master state machine master_fsm 208 enables the digital receiver subsystem dig_rx 216 by asserting a signal rx_go. The digital receiver subsystem dig_rx 216 may enable and receive data from a communication receiver using the rx_en and rx_data signals. In the RX state 304 the master state machine master_fsm 208 similarly waits or holds in this state until an rx_done signal is received indicating that the receiver operations are complete and it then transitions to the CP state 306. In the CP state 306 the master state machine master_fsm 208 enables the charge-pump voltage multiplier controller dig_cp 218 by asserting a signal cp_go to update the state of the charge pump control signals based on the values received from either the digital blink detection subsystem dig_blink 214 or the communication receiver operation dig_rx 216. In this exemplary embodiment, the charge-pump voltage multiplier controller dig_cp 218 requires only one clock cycle to update so that no corresponding done signal is required. The master state machine master_fsm 208 then transitions to the DONE state 308 and remains there until reset by the smclk_rst_n signal.

Figure 4:
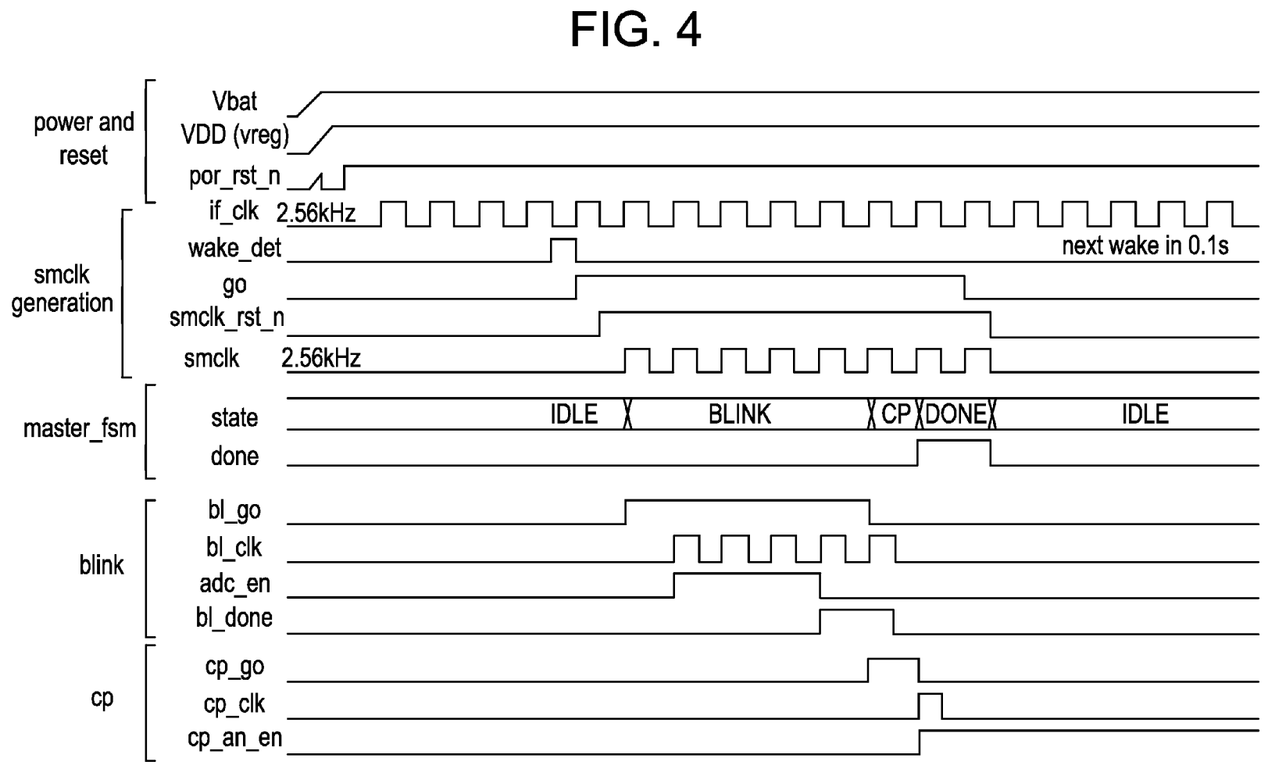
FIG. 4 is a timing diagram of a first exemplary sequence of the operation of the clock and reset generator and master sate machine in accordance with the present invention.

FIG. 4 provides a timing diagram illustrating one of many possible sequences of operations of the clock and reset generator clk_rst_gen 210 and the master state machine master_fsm 208 in accordance with an exemplary embodiment of the present invention. Shown at top are the battery voltage Vbat ramping up to a stable value when a battery or power source is coupled to the system, and then the voltage regulator vreg 200 output signal Vdd or Vreg ramping up to a stable value. Next the regulator based power-on reset vdd_por 204 output signal por_rst_n is asserted, active low, then de-asserted, high, in response to the Vreg voltage. The low frequency oscillator starts, here at a low rate of 2.56 kHz, as shown in the lf_clk signal. Periodically an internal wake signal wake_det is generated, here at an interval of 0.1 seconds, at which time the master state machine reset smclk_rst_n is de-asserted and state machine clocks are provided on the smclk signal. The master state machine master_fsm 208 transitions from its initial IDLE state 300 to the BLINK state 302, and asserts an enable signal bl_go to enable the digital blink detection subsystem dig_blink 214 and the clock signal bl_clk provided by the clk_rst_gen block 210 to the digital blink detection subsystem dig_blink 214. The digital blink detection subsystem dig_blink 214 asserts the signal adc_en to enable an analog-to-digital converter associated with the digital blink detection subsystem dig_blink 214. The adc_en signal may be used further to enable a high-frequency clock source for the analog-to-digital converter when the analog-to-digital converter is active. When the digital blink detection subsystem dig_blink 214 operations are complete the bl_done signal is asserted to the master state machine master_fsm 208 which then disables the bl_go signal thereby resetting the dig_blink state machine 214. As illustrated in this exemplary timing diagram, the system then transitions to the CP state 306 in which the charge pump voltage multiplier controller dig_cp 218 asserts an enable signal cp_an_en to activate the charge pump voltage multiplier 108 (FIG. 1). The cp_an_en signal may be used further to enable a high-frequency clock source for the charge pump voltage multiplier 108 when the charge pump voltage multiplier 108 is active. The master state machine master_fsm 208 then transitions to its DONE state 308 at which point the clock and reset generator clk_rst_gen 210 re-asserts the reset signal smclk_rst_n and disables the state machine clock smclk. It will be appreciated that the sequence illustrated comprises operations that reduce overall system power consumption by enabling clocks and circuits only when necessary.

Figure 5:
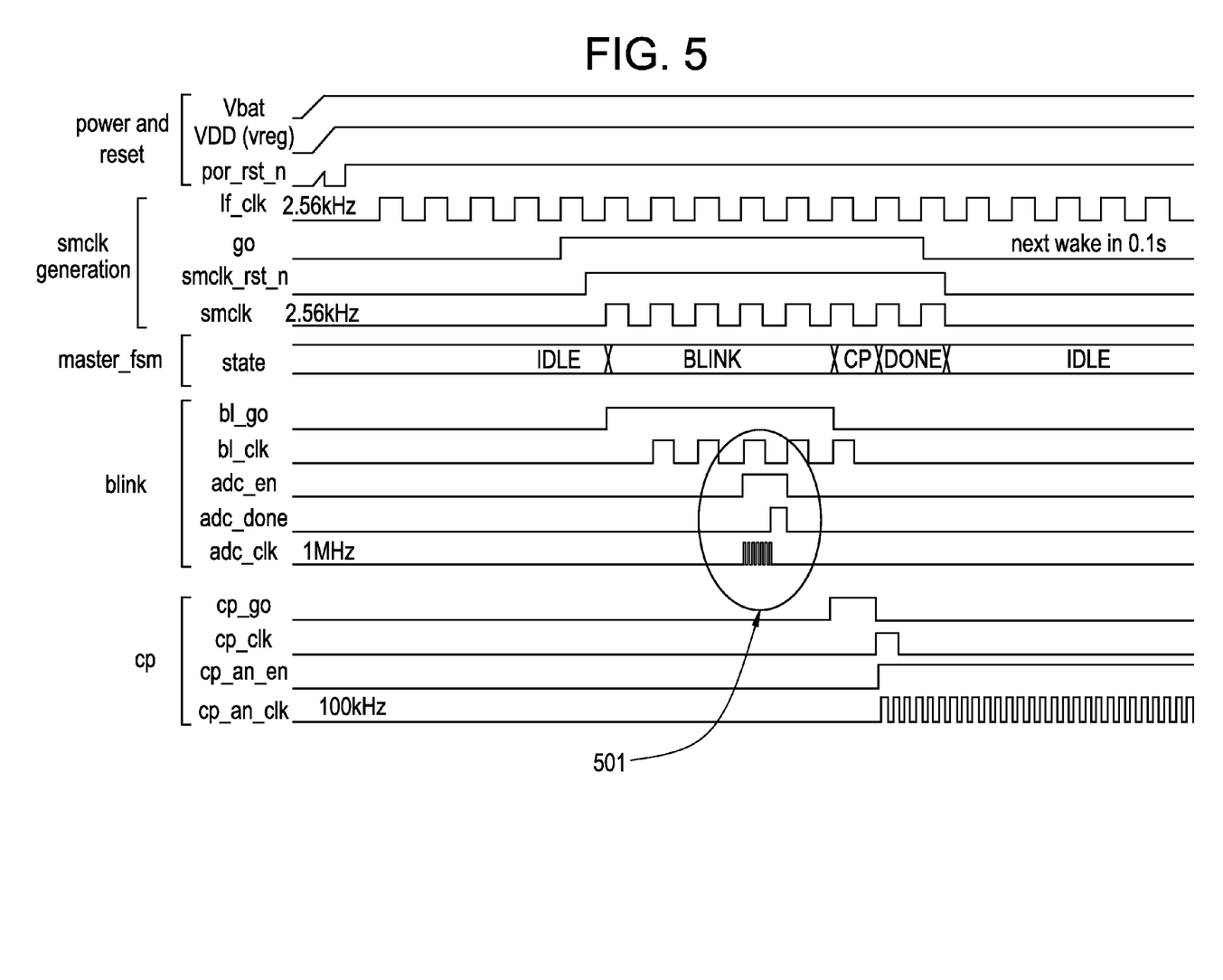
FIG. 5 is a timing diagram of a second exemplary sequence of the operation of the clock and reset generator and master sate machine in accordance with the present invention.

FIG. 5 provides a timing diagram illustrating another of many possible sequences of operations of the clock and reset generator clk_rst_gen 210 and the master state machine master_fsm 208 with additional detail provided for clock signals in accordance with the exemplary system of the present invention. In the BLINK state 302, the adc_en signal provided by the digital blink detection subsystem dig_blink 214 may be used in the sensor signal path to enable a high-speed analog-to-digital converter clock adc_clk. The high speed analog-to-digital converter clock adc_clk may be implemented in the associated sensor signal path or in the clock and reset generator. Also illustrated in FIG. 5 is an adc_done signal provided by the analog-to-digital converter to indicate its operations are complete. In some exemplary embodiments of the present invention, the high-speed analog-to-digital converter clock adc_clk may be disabled or gated off, when the adc_done signal is asserted. In this manner the high-speed analog-to-digital converter clock adc_clk is active for the minimum time required for the analog-to-digital converter to complete its operations. It will be appreciated that gating by the adc_done signal provides for disabling the high-speed analog-to-digital converter clock adc_clk well before the next edge of the state machine clock smclk. For example, in some exemplary embodiments, the analog-to-digital converter completes its operations in thirteen (13) cycles of the high speed analog-to-digital converter clock adc_clk at a rate of 1 MHz. Therefore the high speed analog-to-digital converter clock adc_clk may be disabled within thirteen (13) microseconds after being enabled, a relatively short time after being enabled by the master state machine that operates on a 2.56 kHz or three hundred ninety (390) microsecond clock rate. This behavior is illustrated in the circled portion 501 of the signals adc_en, adc_done and adc_clk where it is sown that the adc_clk signal is enabled when adc_en is asserted (active high) and is disabled when adc_done is asserted (active high) by the analog to digital converter. In some further exemplary embodiments, analog circuits such as comparators, voltage references or current sources may be disabled upon assertion of the adc_done signal. These circuits may consume a relatively large amount of current as compared to the overall desired average current drain of the system, so disabling them as soon as possible may greatly reduce overall power consumption of the lens system. Similarly, the charge pump enable signal cp_an_en provided by the digital charge pump voltage multiplier controller dig_cp 218 may be used in the charge pump voltage multiplier to enable a high-speed charge pump clock cp_an_clk. In this manner the system controller, operating on the low-frequency clock lf_clk, may enable and disable higher speed clocks in the variable focus lens system only when they are required thereby minimizing power consumption. It will be appreciated that the active operations controlled by the master state machine master_fsm 208 require approximately eight (8) clock cycles at 2.56 kHz, or 3.125 ms, out of each 0.1 s interval, a duty cycle of 1:32, such that a low overall power consumption is provided by minimizing the active time of each subsystem.

Figure 5A:
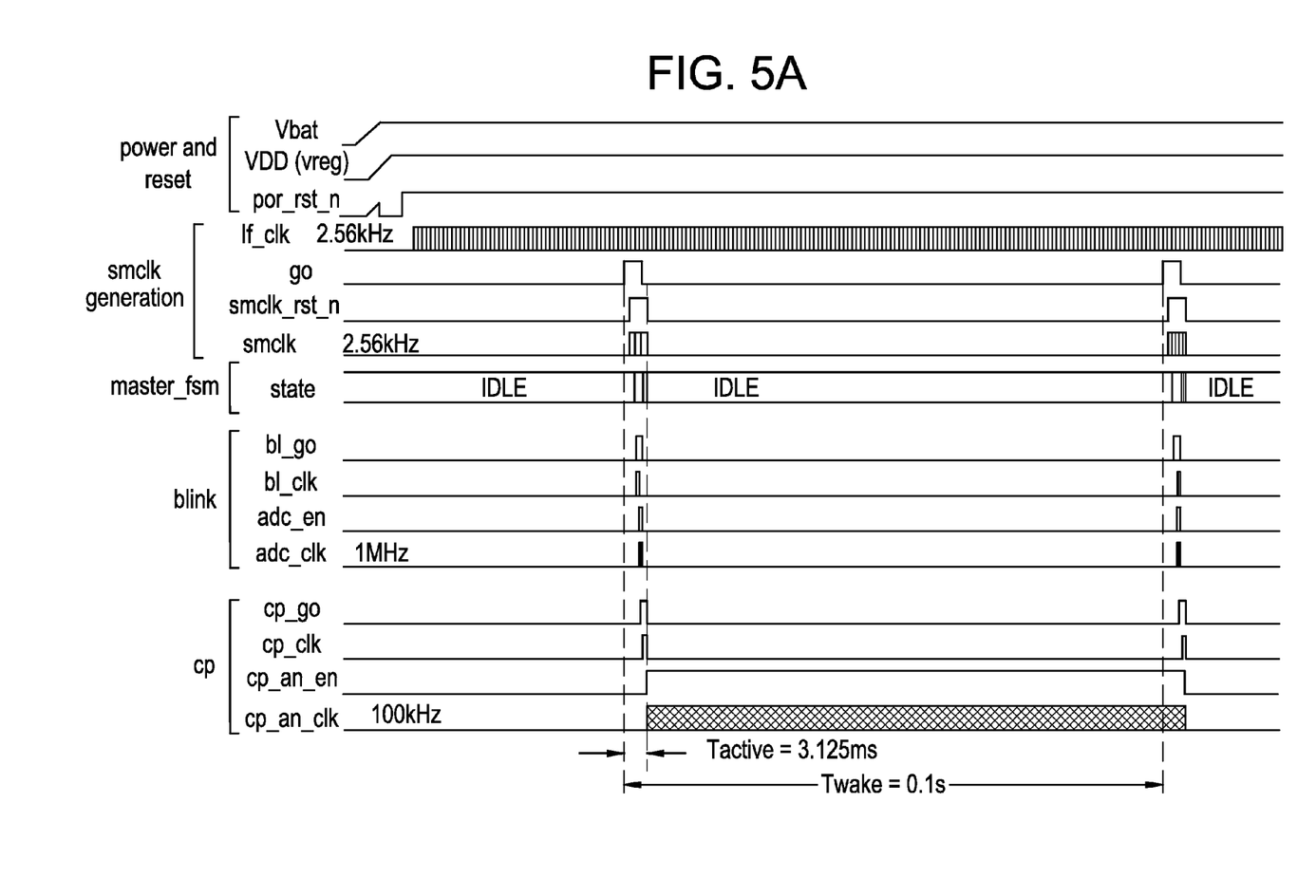
FIG. 5A is an expanded time frame timing diagram of the second exemplary sequence of the operation of the clock and reset generator and master sate machine of FIG. 5 in accordance with the present invention.

FIG. 5A provides an illustration of a set of sequences and operation similar to that illustrated in FIG. 5 over a longer time scale such that a full 0.1 second interval is visible after power up. A first wake up sequence is initiated when the clock and reset generator de-asserts the master state machine reset smclk_rst_n and provides state machine clocks on the smclk signal. The system controller state machines follow a sequence of operations as in FIG. 5 and the operations complete within a duration Tactive of 3.125 milliseconds (ms). As is clear from the illustration, the only active circuits for the remainder of the 0.1 second interval Twake are the voltage regulator, low-frequency clock and counter. A second wake up sequence is initiated at the end of the interval Twake when the clock and reset generator de-assert the master state machine reset smclk_rst_n and provides state machine clocks on the smclk signal.

Figure 6:
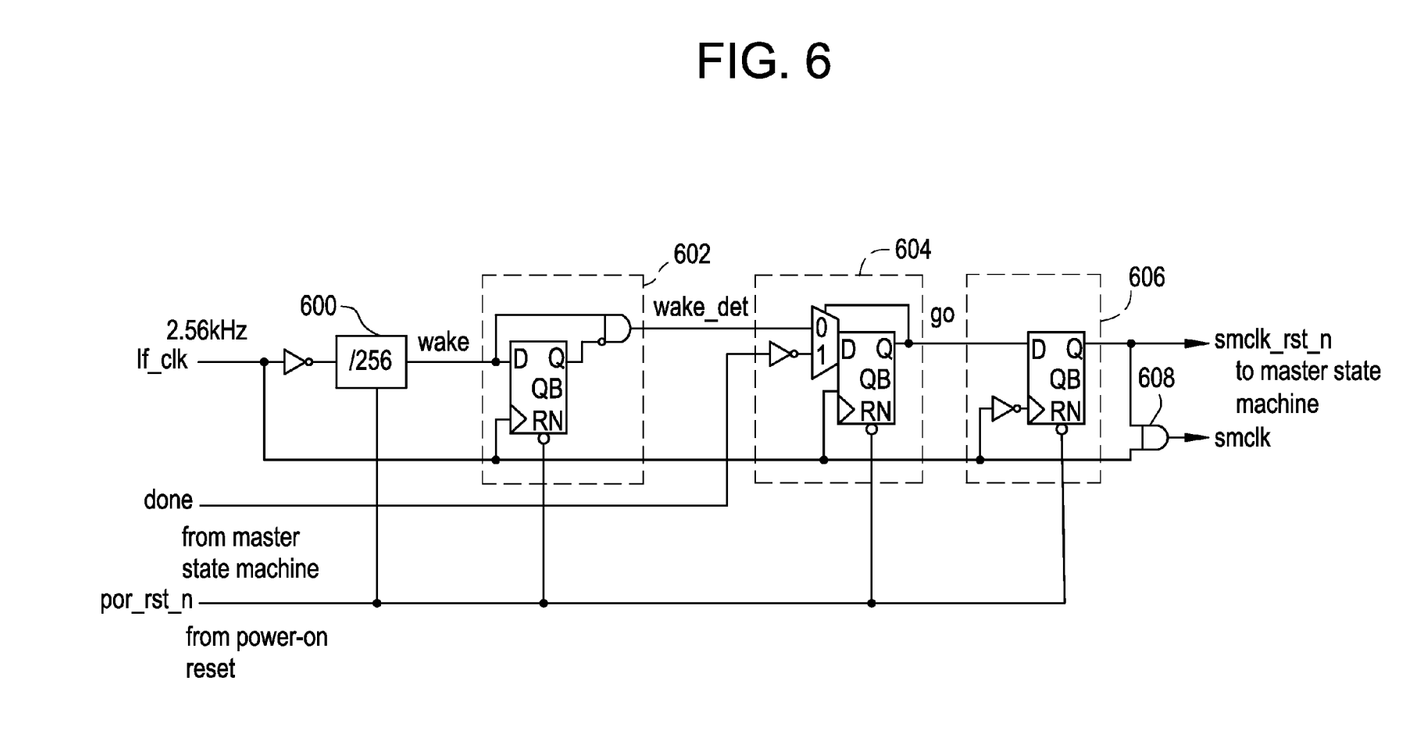
FIG. 6 is a block diagram of a portion of the clock and reset generator of the exemplary control system in accordance with the present invention.

FIG. 6 illustrates an exemplary embodiment of a portion of the clock and reset generator clk_rst_gen 210. The clock and reset generator clk_rst_gen 210 comprises a wake counter 600, a wake detect circuit 602, a go register 604, a state machine enable register 606, and a state machine clock gate 608. When the master state machine master_fsm 208 is in the IDLE state 300 only the low-frequency clock lf_clk and the wake counter 600 are active. Every two hundred fifty-six (256) cycles of the low frequency clock lf_clk the wake counter 600 asserts a wake signal provided to the wake detect circuit 602. The wake detect circuit 602 asserts the wake detect signal wake_det for one cycle of the low frequency clock lf_clk after wake is asserted. The wake counter 600 may operate on falling edges of the low frequency clock lf_clk to maximize hold time at the wake detect circuit 602, for example if the circuit is designed in custom logic. The wake detect signal wake_det is provided to the go register 604. The go register 604 asserts the go signal when wake_det is asserted and holds the go signal in an asserted or active state until the done signal provided by the master state machine master_fsm 208 is asserted. The go signal is provided to the state machine enable register 606. The state machine enable register 606 generates the state machine reset signal smclk_rst_n on the falling edge of the low frequency clock signal lf_clk. The state machine reset signal smclk_rst_n is provided to the master state machine master_fsm 208 and the state machine clock gate 608. The state machine clock gate 608 provides the state machine clock smclk based on the low frequency clock lf_clk when smclk_rst_n is de-asserted. In the illustrated exemplary embodiment, the smclk_rst_n signal is asserted active low and de-asserted to a high level. As illustrated the state machine clock gate 608 may be implemented as an AND gate.

It will be appreciated that enable and clock gating circuits for the blink detection subsystem, the digital receiver subsystem, the charge pump voltage multiplier subsystem and additional subsystems may be implemented in a similar manner to the state machine enable register 606 and the state machine clock gate 608. In this manner the resets, enables and clocks may be generated in a glitch-free manner and to enable the clocks and subsystems only when required thereby minimizing power consumption.

The master state machine, digital subsystem state machines and the clock and reset generator circuits may be constructed with a small set of logic gates and flip flops. As such, the system controller of the present invention may be implemented in a very small area using complementary metal-oxide semiconductor (CMOS) logic circuits on a silicon semiconductor integrated circuit die. Therefore the system controller of the present invention provides the desired functionality to provide flexible control of the electronic systems in an ophthalmic lens in a manner providing minimal power consumption and small area and volume compatible with the requirements for overall size and battery life of the ophthalmic lens.

The logic functions of the system controller may be implemented in sequential digital logic including finite state machines as are well known in the art. It will be appreciated that alternative embodiments are possible, such as implementing several of the algorithms and functions in software executed in a microcontroller. It will be appreciated that further variations on the system are possible such as use of different types of sensors, different detection algorithms and different partitioning of software and hardware and among one or more integrated circuits. In one exemplary embodiment the system controller is fully integrated into a single silicon CMOS integrated circuit die.

Figure 7:
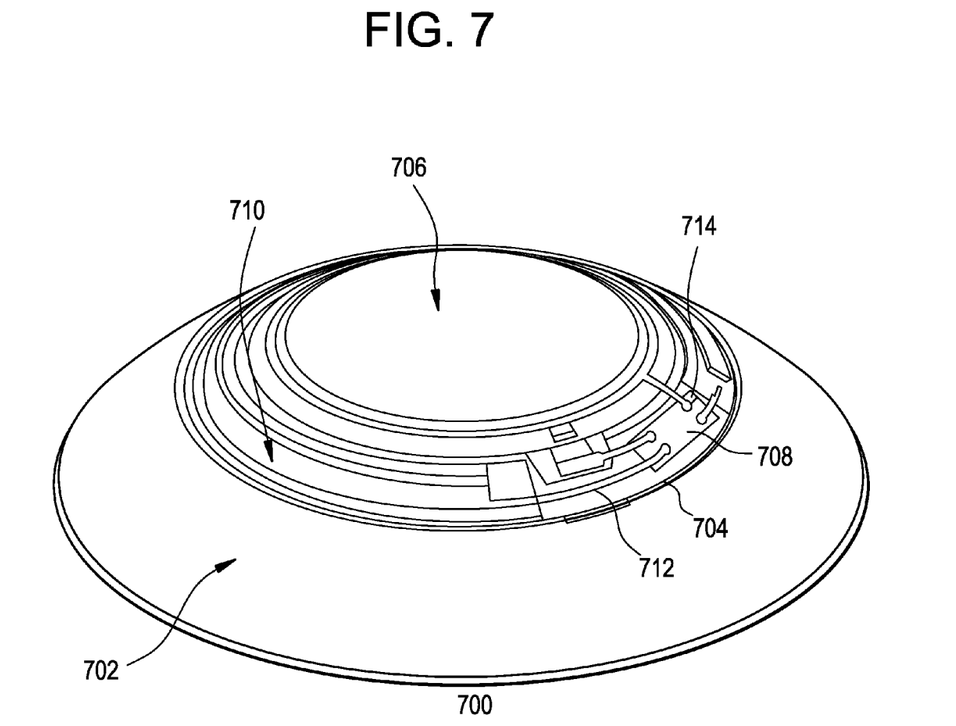
FIG. 7 is a diagrammatic representation of an exemplary electronic insert, including a control system, for a powered contact lens in accordance with the present invention.

Referring now to FIG. 7, there is illustrated an exemplary contact lens with an electronic insert comprising the control system in accordance with exemplary embodiments of the present invention. The exemplary contact lens 700 comprises a soft plastic portion 702 which comprises an electronic insert 704. This electronic insert 704 includes a lens 706 which is activated or controlled by the electronics described herein, for example, focusing near or far depending up activation. Circuitry 708 mounts onto the insert 704 and is connected to a power source 710, such as batteries via one or more electrical interconnect traces 712. Additional circuitry may also be connected via the electrical interconnect traces 712. Circuitry 708 may include any of the components set forth herein, including one or more sensors 714.

In one exemplary embodiment, the electronics and electronic interconnections are made in the peripheral zone of a contact lens rather than in the optic zone. In accordance with an alternate exemplary embodiment, it is important to note that the positioning of the electronics need not be limited to the peripheral zone of the contact lens. All of the electronic components described herein may be fabricated utilizing thin-film technology and/or transparent materials. If these technologies are utilized, the electronic components may be placed in any suitable location as long as they are compatible with the optics.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An ophthalmic apparatus comprising:
   an ophthalmic device including a soft plastic portion having an electronic insert comprising a variable-focus lens in the center thereof;
   an electronic system incorporated into the ophthalmic device and configured for use in at least one of in or on the eye, the electronic system mounted on the electronic insert around the variable-focus lens;
   a system controller incorporated into the electronic system for controlling the operation thereof, the system controller being configured to implement a master state machine that receives a master state machine clock signal and outputs at least one signal, the system controller including a clock and reset subsystem and at least one subsystem configured to implement a subsystem state machine to control an electronic component of the electronic system, wherein the master state machine progresses through a predetermined sequence of states, and wherein the clock and reset generator subsystem and master state machine interoperate to supply a state machine clock signal and an enable signal operable to activate and then deactivate the at least one subsystem upon completion of the subsystem's operation to reduce power consumption, a subsystem clock signal being at a higher frequency than the master state machine clock signal;
   electronic circuitry incorporated into the electronic system, the electronic circuitry being operatively associated with and providing power to the system controller, the electronic circuitry including one or more power sources and one or more of clock generation circuits or inputs; and
   at least one actuator configured to receive the at least one output from the system controller to control the operation of the variable-focus lens.

2. The ophthalmic apparatus according to claim 1, wherein the ophthalmic device comprises a contact lens.

3. The ophthalmic apparatus according to claim 2, wherein the contact lens comprises a soft contact lens.

4. The ophthalmic apparatus according to claim 1, wherein the master state machine is implemented in hardware.

5. The ophthalmic apparatus according to claim 1, wherein the master state machine is implemented in software.

6. The ophthalmic apparatus according to claim 1, wherein the master state machine is implemented in a combination of hardware and software.

7. The ophthalmic apparatus according to claim 1, wherein the clock and reset generator subsystem comprises a low-frequency clock source and counter.

8. The ophthalmic apparatus according to claim 7, wherein the system controller is configured to have only the low-frequency clock source and counter in an active state upon a reset, at a startup, and/or between a sampling and an actuation action.

9. The ophthalmic apparatus according to claim 1 wherein the clock and reset generator circuit is configured to provide a state machine clock and a state machine reset to the master state machine and periodically activate the master state machine.

10. The ophthalmic apparatus according to claim 1, further comprising a first sensor and a first sensor signal path, wherein the master state machine is configured to periodically enable the first sensor and the first sensor signal path and receive a sensor signal having a value or sequence of values, and wherein the activation period corresponds to a predetermined sample rate of the first sensor and first sensor signal path.

11. The ophthalmic apparatus according to claim 10, further comprising a second sensor and a second sensor signal path, wherein the master state machine is configured to enable the second sensor and the second sensor signal path upon detecting a unique predetermined value or sequence of values from the first sensor and first sensor signal path.

12. The ophthalmic apparatus according to claim 11, wherein the first sensor and the first sensor signal path comprises a photosensor and photosensor signal path and the sensor signal comprises a value indicating an incident light level on the photosensor.

13. The ophthalmic apparatus according to claim 12, wherein the predetermined sequence of values represents a blink pattern.

14. The ophthalmic apparatus according to claim 13, wherein the master state machine enables a lens driver upon detection of a first blink pattern.

15. The ophthalmic apparatus according to claim 14, wherein the master state machine enables at least one of a light or electromagnetic receiver upon detection of a second blink pattern.

16. The ophthalmic apparatus according to claim 15, wherein the electronic system further comprises a subsystem having a high-speed clock configured to provide a "done" signal indicating completion of its operations to the master state machine.

17. The ophthalmic apparatus according to claim 1, wherein the electronic circuitry further comprises power management circuitry.

18. The ophthalmic apparatus according to claim 1, wherein the electronic circuitry further comprises one or more high voltage generators.

19. The ophthalmic apparatus according to claim 1, wherein the electronic circuitry further comprises one or more switching circuits.

20. The ophthalmic apparatus according to claim 1, wherein the electronic circuitry further comprises one or more sensors.

21. The ophthalmic apparatus according to claim 1, wherein the at least one subsystem comprises a digital blink detection subsystem.

22. The ophthalmic apparatus according to claim 1, wherein the at least one subsystems comprises a charge pump voltage multiplier controller subsystem.

23. The ophthalmic apparatus according to claim 1, wherein the at least one subsystem comprises a digital receiver subsystem.

24. An ophthalmic apparatus comprising:
- an ophthalmic device including a soft plastic portion having an electronic insert comprising a variable-focus lens in the center thereof;
- an electronic system incorporated into the ophthalmic device and configured for use in at least one of in or on the eye, the electronic system mounted on the electronic insert around the variable-focus lens;
- a system controller incorporated into the electronic system for controlling the operation thereof, the system controller being configured to implement a master state machine that receives a master state machine clock signal and outputs at least one signal, the system controller including a clock and reset subsystem and at least one subsystem configured to implement a subsystem state machine to control an electronic component of the electronic system, wherein the master state machine progresses through a predetermined sequence of states, and wherein the subsystem receives a subsystem clock signal having a higher frequency than the master state machine clock signal and wherein the subsystem generates a done signal operable to disables the subsystem clock signal upon completion of the subsystem's operation to reduce power consumption;
- electronic circuitry incorporated into the electronic system, the electronic circuitry being operatively associated with and providing power to the system controller, the electronic circuitry including one or more power sources and one or more of clock generation circuits or inputs; and
- at least one actuator configured to receive the at least one output from the system controller to control the operation of the variable-focus lens.

* * * * *